United States Patent [19]

Steer

[11] Patent Number: 4,603,837

[45] Date of Patent: Aug. 5, 1986

[54] TAP OR VALVE

[75] Inventor: Peter L. Steer, Surrey, England

[73] Assignee: Craig Medical Products, Limited, England

[21] Appl. No.: 758,911

[22] Filed: Jul. 25, 1985

[30] Foreign Application Priority Data

Aug. 15, 1984 [GB] United Kingdom ............... 8420700

[51] Int. Cl.$^4$ ............................................. F16K 31/00
[52] U.S. Cl. ................................... 251/352; 251/345; 604/248
[58] Field of Search ............... 251/343, 344, 345, 352, 251/310; 604/248, 323; 222/48, 189, 484; 137/218

[56] References Cited

U.S. PATENT DOCUMENTS

| 680,447 | 8/1901 | Swedin | 251/352 |
| 1,091,048 | 3/1914 | Drew | 251/345 |
| 2,755,652 | 7/1956 | Shelton et al. | 251/352 |
| 3,057,350 | 10/1962 | Cowley | 604/248 |
| 3,977,409 | 8/1976 | Brendling | 251/342 |
| 4,055,179 | 10/1977 | Manschot et al. | 251/352 |
| 4,244,363 | 1/1981 | Moore, Jr. et al. | 128/205.17 |
| 4,462,510 | 7/1984 | Steer et al. | 137/218 |

FOREIGN PATENT DOCUMENTS 1201636 8/1970 United Kingdom .

Primary Examiner—A. Michael Chambers
Attorney, Agent, or Firm—Lawrence S. Levinson; Sanford J. Asman

[57] ABSTRACT

The tap or valve is made up of a first tube and a second tube which may be located about a common axis. Each of the tubes has a portion of its wall extending around only a part of its periphery, cut away. One of the tubes is rotatable between an "open position" in which the apertures wholly or partly overlap and a "closed position" in which the apertures are overlapped by a portion of the tube.

5 Claims, 7 Drawing Figures

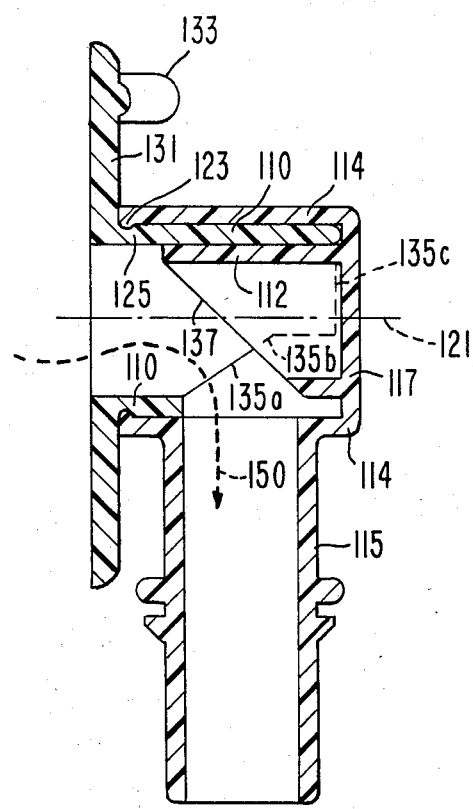
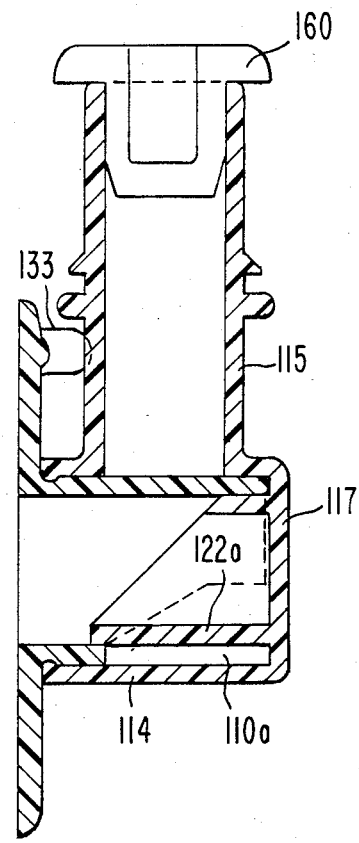
Fig. 4.
Fig. 5.
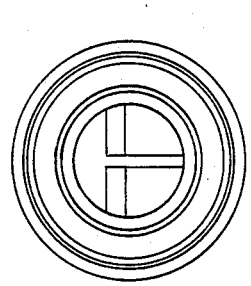
Fig. 3.
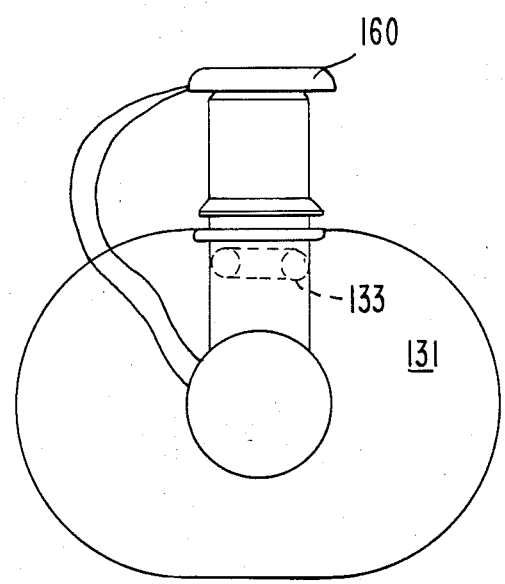
Fig. 6.

TAP OR VALVE

BACKGROUND OF THE INVENTION

The present invention relates to a tap or valve. The tap or valve particularly described and illustrated herein is intended for use in urine drainage tubing or use on a urine drainage bag, but the present invention is not limited to these applications. A compact and easily manufactured tap or valve which does not leak can be advantageously used in a wide variety of applications.

One design of tap for a drainage bag is disclosed in U.S. Pat. No. 4,462,510 entitled TAP FOR DRAINAGE BAG which issued to Peter L. Steer and John V. Edwards on July 31, 1984, and while this tap has a number of technically advantageous features, it would be desirable to have available a simple design of tap in which the likelihood of leakage is minimized.

British Pat. No. 1 201 636 describes a valve for installation in a hot water radiator in which one length of a pipe within the radiator has an end portion embodying an oblique edge, and another length of pipe within the radiator also has an end portion embodying an oblique edge. One of the pipe end portions contitutes a socket into which the other pipe's end portion fits. The pipe lengths are mutually located and relatively rotatable, such that by turning of one relative to the other the size of a lateral opening defined by the mutually opposed oblique edges is regulated.

SUMMARY OF THE INVENTION

A tap or valve of simple and reliable construction for use primarily, but not exclusively, in urine drainage tubing or on a urine drainage bag has been designed.

According to one aspect of the present invention, a tap or valve which includes a first tube and a second tube which are relatively rotatable about a common axis is provided. Each of the tubes has a portion of its wall, extending around only a part of the periphery of the respective tube, cut away. One of the two tubes is rotatable relative to the other between an "open" position, in which the apertues defined by the cutaway portions overlap partly or wholly, and a "closed" position, in which the aperture defined by a cutaway portion of each of said first and second tubes is overlapped by a portion of the wall of the other of tube, wherein said second tube is mounted within a third external tube and the first tube fits relatively rotatably within the external tube while the second tube fits snuggly, but relatively rotatably, within the first tube.

In a preferred embodiment of the invention, the cutaway portion of one tube, herein called "the first tube" is defined by a plane which intersects the tube at an angle, e.g. from 30 to 60 degrees, to the tube axis. Such a tube may be arranged to cooperate with the second tube, which is in the form of a stub or spigot mounted within the external tube and which has a cutaway portion defined by a plane which intersects the stub or spigot at an angle (e.g. 30 to 60 degree) to the axis of the stub or spigot. The first tube preferably fits snugly within the external tube.

The tap or valve according to the invention is preferably constructed from plastic, since it is possible to obtain a very close, and, hence, substantially leak-free, fit between the parts of the tap or valve using plastic.

In another aspect, the invention provides a urine drainage device, such as a tube or bag, incorporating a tap or valve according to the invention.

BRIEF DESCRIPTION OF THE DRAWING

In the drawing:

FIG. 3 is an under plan view corresponding to FIG. 1.; and

FIGS. 4, 5, 6 and 7 show a second example of a tap or valve according to the invention, particularly suitable for attachment to a urine bag, FIG. 4 being an axial cross-section showing the valve in its open position, FIG. 5 being a similar view showing it in its closed position, FIG. 6 being a front view, and FIG. 7 being a top plan view.

DETAILED DESCRIPTION OF THE PREFERRED EMBODIMENT

In its simpliest embodiment, a valve according with the invention is made up from two tubes which are relatively rotatable about a common axis within a third external tube. The first and second tubes partly overlap and one fits inside the other. A part of the wall of each tube is cut away, thereby defining an aperture in the wall of each tube. These apertures are positioned and dimensioned so that, with the tubes in one relaive rotary position, the aperture in each tube is closed off by a wall of the other tube, whereas, in another rotary position, these apertures partly or wholly coincide, thereby providing an exit path for fluid within the interior of the inner tube through to the external tube. The cutaway portion of the wall of each tube may be defined by a plane at an angle, e.g., 45 degrees to a common axis of the tubes. A different configuration of cutaway portion may be employed. It is not necessary that the angle of the intersecting plane is of any particular value, but if the intersecting plane is at two small an angle to the common axis of the tubes, then the valve will occupy a considerable length of the tube, whereas if the itersecting plane is a large angle, for example 75–85 degrees to the common axis of the tubes, then the cross-sectional area (maximum) of the flow path when the valve is open is small and hence the maximum flow capacity of the value is limited.

Figure 1:
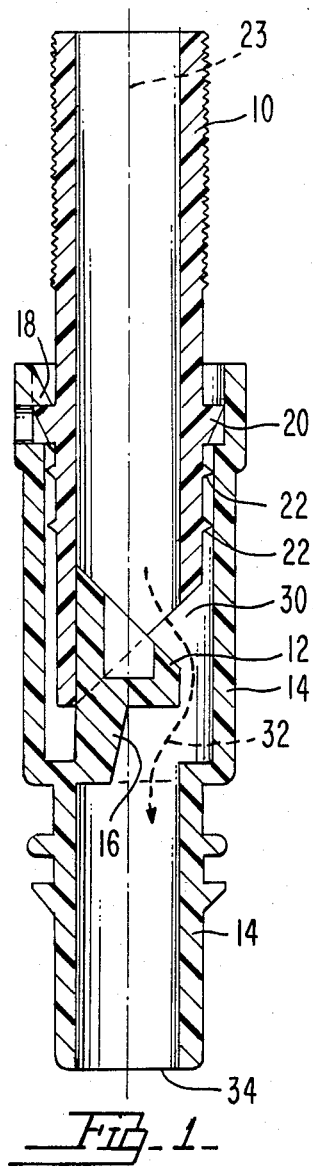
FIGS. 1 and 2 are axial cross-sectional views of a first example of tap or valve in accordance with the invention, FIG. 2 showing the valve in its closed position and FIG. 1 showing the valve in its open position.
Figure 2:
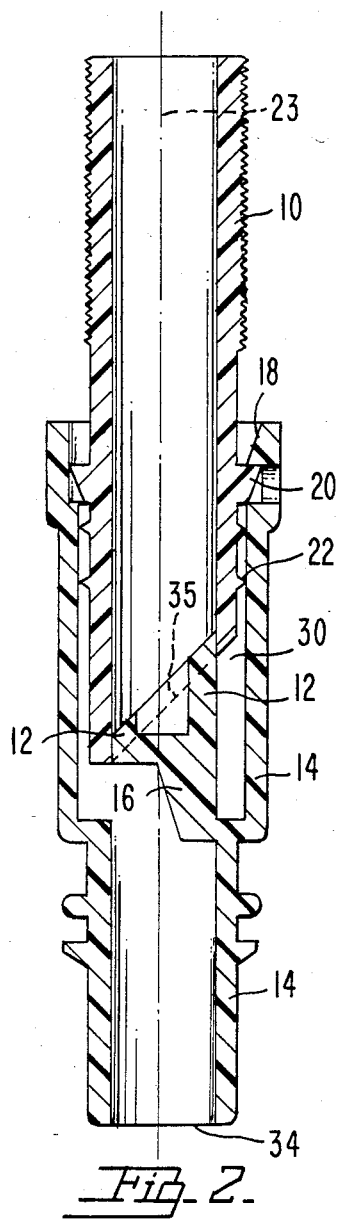

Referring now to FIGS. 1–3, the illustrated valve includes a first tube 10 which cooperates with a spigot or second tube 12, the latter being located within an external or third tube 14. The spigot 12 is integral with the external tube 14, being joined thereto by a support web 16. The first tube 10 is generally restrained against longitudinal axial movement relative to the external tube 14 and hence relative to the spigot 12. This restraint, in the embodiment illustrated in FIGS. 1–3, is achieved by inwardly directed detents, one of which is seen at 18, extending inwardly from the external tube 14. These detents cooperate with a peripheral rib 20 on the first tube 10. On its outer surface, the first tube 10 has a pair of peripheral ribs 22, which serve as bearings mounting the tube 10 for rotation about the common axis 23 of the tubes within the outer tube 14. However, these external ribs 22 are not essential, and they may be omitted.

The operations of the illustrated valve can be seen by comparing FIGS. 1 and 2. As shown in FIG. 2, the valve is closed, in that the spigot or second tube 12 blocks off the open portion of the end of the first tube 10. In order to open the valve, the second tube 12 and the external tube 14 are rotated through substantially 180 degrees relative to the first tube 10 to take the position illustrated in FIG. 1. In this position the cutaway region 30 of the wall of the tube is not closed off by the spigot 12, and fluid is able to flow along the path indicated by the dashed arrow 32 and out the open end 34 of the valve.

While the end of the tube 10 has been cut by a plane substantially at an angle of 45 degrees relative to the common axis 23 of the tubes, it will be appreciated that other angles could be employed. It is preferred, however, that the angle of the intersecting plane 35 should be between about 30 degrees and about 60 degrees.

For better sealing, it may be arranged that the outside diameter of the spigot or second tube 12 is a few thousands of an inch (a few hundredths of a millimeter) larger than the inside diameter of the first tube 10, so that there is an interference fit between these parts. However, it is preferred that the interference fit between these parts is not so tight that relative rotation by manual manipulation is made impossible. However, in some embodiments, a tight interference fit at this point may be desirable where a lever or other means of obtaining a mechanical advantage is employed to rotate the second tube 12 and third tube 14 relative to the first tube 10.

A number of variations on this basic concept are possible. As shown in FIGS. 1 and 2, the intersecting plane 35 extends across the whole of the internal tubular space, but in other embodiments of the invention the end of the first tube 10 and/or the end of the second tube 12 can be defined by a first plane transverse to the common axis of the tubes and a second plane at an angle thereto. This arrangment may be advantageous in certain embodiments in that a greater area of confronting surface to surface contact is obtained between the outer and inner surfaces of the first tube 10 and the confronting inner surface of the external tube 14 and outer surface of the spigot or second tube 12.

A further illustrative embodiment of the invention is shown in FIGS. 4–7. The tap illustrated in FIGS. 4–7 has a first tube 110, a spigot or second tube 112, and an external tube 114. A lateral exit pipe 115 is made integral with the external tube 114. The end of the tube 114 is closed by a wall 117. The external tube 114 can rotate relative to the tube 110 about a common axis 121. As illustrated, an inwardly directed rim 123 cooperates with a shallow groove or channel 125 at the root end of the tube 110, to provide a detent arrangement by which the composite member comprising tubes 112 and 114 is maintained on the tube 110, while these two parts are free to rotate relatively.

A flange 131 is integral with the tube 110. This flange 131 serves for attaching the tap to a wall of a urine bag, or may alternatively be used to attach the tap to any container from which exit of liquid is to be controlled. It will be appreciated that an arrangement of this kind could be utilized, e.g. for controlling the flow of wine out of a wine bag or controlling the flow of beer out of a beer can or barrel.

Figure 7:
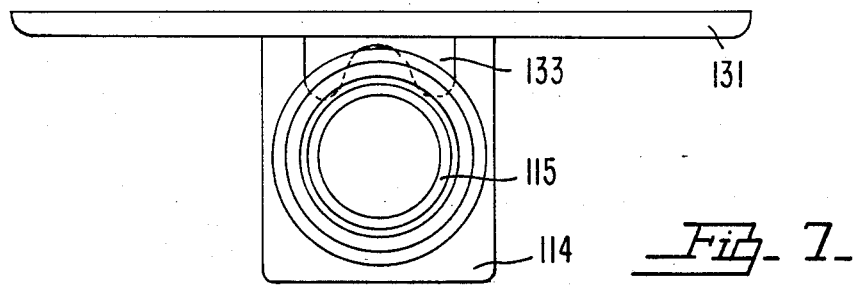

A saddle-shaped member 133, seen best in FIGS. 4 and 7 is fixed to the flange 131 and is made of deformable material. Its function is to maintain the pipe 115, when desired, in a vertical position as seen in FIG. 5 which corresponds to the closed position of the tap or valve.

As illustrated, the spigot 112 is hollow but it could be solid. One end of the spigot is defined by an inclined planar surface the plane being indicated at 137. The tube 110 has a portion of its wall cut away, its edge being indicated at 135, and it will be seen that the cut away portion is defined by an inclined plane 135a, a straight edge 135b and an edge 135c transverse to the commons axis 121.

The operation of the valve may readily be understood by comparing FIGS. 4 and 5. FIG. 4 illustrates the open position of the valve in which a liquid exit flow path is indicated at 150. FIG. 5 illustrates the closed position of the valve in which the pipe 115 is held vertical by the detent 133 and in this position it is seen that the wall portion 112a of the spigot or second tube 112 closes off the aperture 110a in the first tube 110. As an optional feature, and as seen in FIGS. 5 and 6, a stopper 160 may be inserted in the end of the tube 115. As mentioned, the tap or valve works the same way if the spigot 112 is solid, rather than hollow, as illustrated.

In a preferred embodiment of the invention, the flange 131 and tube 110 may be made of a rigid plastic, such as PVC, and the spigot 112, the external tube 114, and the pipe 115 may be made of a slightly resilient synthetic plastic material, such as high density polyethylene. Other materials, however, may be used. The invention is not regarded as limited to the use of any particular plastic material.

I claim:

1. A tap or valve which includes a first tube and a second tube which are relatively rotatable about a common axis, each of said first and second tubes having a portion of its wall cut away, said portion extending around only a part of the periphery of the respective tube, and one of said first and second tubes being rotatable relative to the other between an "open" position in which the apertures defind by the cutaway portions overlap partly or wholly and a "closed" position in which the aperture defined by a cutaway portion of each of said first and second tubes is overlapped by a portion of the wall of the other of said first and second tubes, wherein said second tube is mounted internally of a third external tube and said first tube fits relatively rotatably within the external tube while said second tube fits snuggly, but relatively rotatably, within said first tube.

2. The tap or valve of claim 1 wherein the cutaway portion of the first tube is that served by a plane which intersects said tube at an angle to the axis of said tube.

3. The tap or valve of claim 2 wherein the first tube is arranged to cooperate with said second tube in the form of a stub or spigot which is mounted within said external tube and which has a cut away portion defined by a plane which intersects said stub or spigot at an angle to the axis of said stub or spigot.

4. The tap or valve of claim 3 wherein the first tube fits snuggly within said external tube.

5. The tap or valve of claim 4 constructed from plastic.

* * * * *